United States Patent
Novak et al.

(10) Patent No.: US 11,104,650 B2
(45) Date of Patent: Aug. 31, 2021

(54) PROCESS FOR PRODUCTION OF 2-CHLORO-4-NITROIMIDAZOLE DERIVATIVES

(71) Applicant: OTSUKA PHARMACEUTICAL CO., LTD., Tokyo (JP)

(72) Inventors: Petr Novak, Uvaly (CZ); Petr Zahradnik, Chomutov (CZ); Jiri Tauchman, Prague (CZ); Jan Koci, Prelouc (CZ); Antonin Sturc, Prague (CZ)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/965,464

(22) PCT Filed: Jan. 29, 2018

(86) PCT No.: PCT/JP2018/002759
§ 371 (c)(1),
(2) Date: Jul. 28, 2020

(87) PCT Pub. No.: WO2019/146113
PCT Pub. Date: Aug. 1, 2019

(65) Prior Publication Data
US 2021/0053925 A1    Feb. 25, 2021

(51) Int. Cl.
*C07D 233/92*    (2006.01)

(52) U.S. Cl.
CPC .................. *C07D 233/92* (2013.01)

(58) Field of Classification Search
None
See application file for complete search history.

(56) References Cited

U.S. PATENT DOCUMENTS

| 2007/0161802 A1 | 7/2007 | Shinhama |
| 2009/0082575 A1 | 3/2009 | Shinhama |
| 2011/0178308 A1 | 7/2011 | Wuellner et al. |

FOREIGN PATENT DOCUMENTS

| CN | 103396369 A | 11/2013 |
| CN | 103396369 B | 3/2016 |
| WO | 2005/077913 A1 | 8/2005 |
| WO | 2006/035960 A2 | 4/2006 |
| WO | 2010/021409 A1 | 2/2010 |
| WO | 2010/143007 A1 | 12/2010 |

OTHER PUBLICATIONS

Suwinski et al., "Nitroimidazoles. Part V. Chloronitroimidazoles From Dinitroimidazoles. A Reinvestigation", Polish Journal of Chemistry, 1982, vol. 56, pp. 1261-1272 (12 pages total).
International Search Report dated Apr. 17, 2018 issued by the International Searching Authority in International Application No. PCT/JP2018/002759.
International Preliminary Report on Patentability with the translation of Written Opinion dated Aug. 4, 2020 issued by the International Bureau in International Application No. PCT/JP2018/002759.

*Primary Examiner* — Samantha L Shterengarts
(74) *Attorney, Agent, or Firm* — Sughrue Mion, PLLC

(57) ABSTRACT

An improved process for preparing 2-chloro-4-nitroimidazole derivatives which are useful intermediates in the preparation of an anti-tuberculosis drug is provided. The process may comprise the step of chlorinating nitroimidazoles with a chlorinating agent and an activating agent to give 2-chloro-4-nitroimidazole derivatives.

16 Claims, No Drawings

PROCESS FOR PRODUCTION OF 2-CHLORO-4-NITROIMIDAZOLE DERIVATIVES

This application is a National Stage of International Application No. PCT/JP2018/002759 filed Jan. 29, 2018.

TECHNICAL FIELD

The present invention relates to an improved process for preparing 2-chloro-4-nitroimidazole derivatives which are useful intermediates in the preparation of an anti-tuberculosis drug.

BACKGROUND ART

2-Chloro-4-nitroimidazole (also referred to as "2-CNI" hereinafter) is one of useful intermediates in the preparation of an anti-tuberculosis drug, delamanid (chemical name: (2R)-2-methyl-6-nitro-2-[(4-{4-[4-(trifluoromethoxy)phenoxy]-1-piperidinyl}phenoxy)methyl]-2,3-dihydroimidazo[2,1-b][1,3]oxazole):

[Chem. 1]

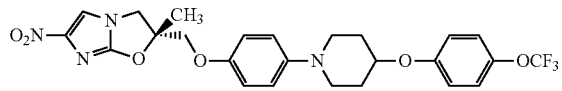

Delamanid is useful for the treatment of multidrug resistant lung tuberculosis.

A number of methods for synthesis of 2-CNI have been already reported, which include various approaches. Most of them, however, have any various disadvantages, e.g. risk of explosion, toxicity, and high overall production costs.

A process for production of 2-CNI is disclosed in Polish Journal of Chemistry 1982, 56, 1261-1272, which is a process via nitration. However, the manufacturing process has a major problem in terms of its safety, i.e., some of intermediates such as dinitroimidazoles are not stable and can cause an explosion. WO 2010/021409 discloses several optimized processes for production of 2-CNI via nitration as shown below. The process is economically advantageous, but the safety risks in the synthesis and process still persist.

[Chem. 2]

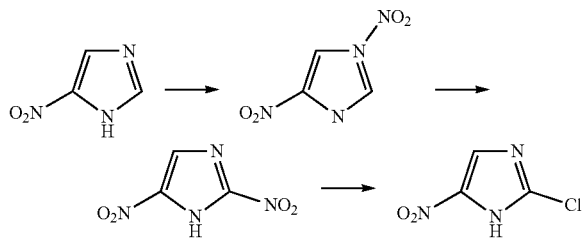

An alternative process of preparing 2-CNI by nitrating 2-chloroimidazole is disclosed in CN 103396369A, but the process brings down several disadvantages such as use of a nitrating mixture as shown below (e.g. fuming nitric acid and fuming sulfuric acid) and higher costs associated with the special reaction materials.

[Chem. 3]

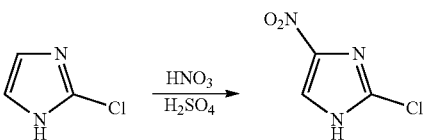

In another approach, 2-chloro-4-nitroimidazole is prepared via N-protected 4-nitroimidazole (WO 2006/035960, as shown below). 2-Bromo-5-halo-4-nitroimidazole is protected under alkoxyalkylation, followed by selective reduction to the corresponding 1-alkoxyalkyl-2-bromo-4-nitroimidazole. And then, the treatment of 1-alkoxyalkyl-2-bromo-4-nitroimidazole with hydrochloric acid affords 2-chloro-4-nitroimidazole. However, it is a long process.

[Chem. 4]

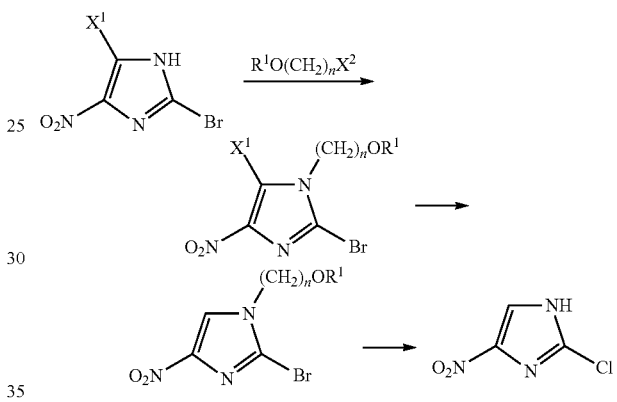

In the scheme, $R^1$ is lower alkyl, n is an integer of 1 to 3, $X^1$ is halogen, and $X^2$ is halogen or lower alkoxy.

Another method disclosed in US 2007/0161802 A1 comprises iodinating 4-nitroimidazole compounds and then reducing the obtained 5-iodo-4-nitroimidazole compounds to produce 2-halogenated 4-nitroimidazole compounds as shown below.

[Chem. 5]

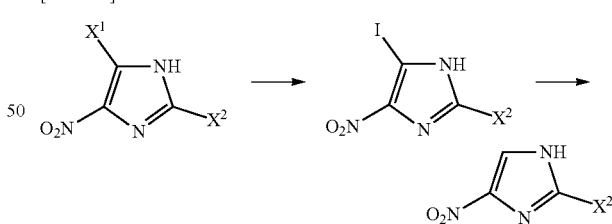

In the scheme, each of $X^1$ and $X^2$ is independently chlorine or bromine.

Efficient selective chlorination of 4-nitroimidazoles is not known and a further efficient process for preparing 2-chloro-4-nitroimidazole derivatives is desired.

CITATION LIST

Patent Literature

[PTL 1] WO 2010/021409
[PTL 2] CN 103396369A

[PTL 3] WO 2006/035960
[PTL 4] US 2007/0161802

Non Patent Literature

[NPL 1] Polish Journal of Chemistry 1982, 56, 1261-1272

SUMMARY OF INVENTION

Technical Problem

An improved process for preparing 2-chloro-4-nitroimidazole derivatives which are useful intermediates in the preparation of an anti-tuberculosis drug, Delamanid, is provided.

Solution to Problem

The inventors have extensively studied to improve a process for preparing 2-chloro-4-nitroimidazole derivatives and then have developed and achieved efficient processes for production of 2-chloro-4-nitroimidazole derivatives via selective chlorination with a suitable chlorinating agent in combination with an activating agent.

The processes disclosed herein include the following embodiment:
A process for preparing a compound of Formula I:

[Chem. 6]

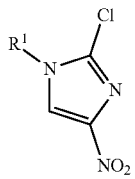

I wherein $R^1$ is selected from the group consisting of $C_{1-6}$ alkoxy-$C_{1-6}$ alkyl, $C_{1-6}$ alkoxy-$C_{1-6}$ alkoxy-$C_{1-6}$ alkyl, $C_{1-6}$ alkanoyloxymethyl, $C_{6-14}$ aralkyl, $C_{6-10}$ aryloxy-$C_{1-6}$ alkyl, $C_{1-6}$ alkoxycarbonyl, $C_{6-10}$ arylcarbonyl, $C_{1-6}$ alkylsulfonyl, $C_{1-6}$ alkyl-$C_{6-10}$ arylsulfonyl, and tetrahydropyranyl, each of which may be optionally substituted with at least one halogen atom, comprising chlorinating a compound of Formula II:

[Chem. 7]

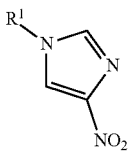

II with a chlorinating agent and an activating agent to give a compound of Formula I.

Advantageous Effects of Invention

The processes disclosed herein may have at least one of the following advantages:

Selective chlorination may be achieved by selecting a suitable chlorinating agent in combination with a suitable activating agent;

Such selective chlorination may reduce unreacted starting materials which may be difficult to be separated or generation of by-products;

Chlorination products may not be extremely harmful;

The procedures during the processes may be also easy and workable on an industrial scale; and Low production costs may allow the processes to be economically reasonable.

DESCRIPTION OF EMBODIMENTS

One aspect of the present invention includes the following embodiments:
(Item 1)
A process for preparing a compound of Formula I:

[Chem. 8]

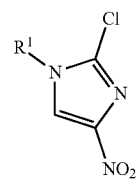

I wherein $R^1$ is selected from the group consisting of $C_{1-6}$ alkoxy-$C_{1-6}$ alkyl, $C_{1-6}$ alkoxy-$C_{1-6}$ alkoxy-$C_{1-6}$ alkyl, $C_{1-6}$ alkanoyloxymethyl, $C_{6-14}$ aralkyl, $C_{6-10}$ aryloxy-$C_{1-6}$ alkyl, $C_{1-6}$ alkoxycarbonyl, $C_{6-10}$ arylcarbonyl, $C_{1-6}$ alkylsulfonyl, $C_{1-6}$ alkyl-$C_{6-10}$ arylsulfonyl, and tetrahydropyranyl, each of which may be optionally substituted with at least one halogen atom, comprising chlorinating a compound of Formula II:

[Chem. 9]

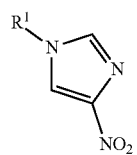

II with a chlorinating agent and an activating agent to give a compound of Formula I.
(Item 2)
The process of Item 1, wherein $R^1$ is selected from $C_{1-6}$ alkoxymethyl, $C_{1-6}$ alkoxycarbonyl, benzyl, phenyloxymethyl, and tetrahydropyranyl, each of which may be optionally substituted with at least one halogen atom.
(Item 3)
The process of either of Item 1 or 2, wherein the chlorinating agent is a 5 or 6-membered heteromonocycle comprising one or more of the following chloroimide moiety in the ring:

[Chem. 10]

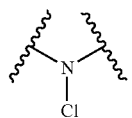

(Item 4)

The process of either of Item 1 or 2, wherein the chlorinating agent is a 5 or 6-membered heteromonocycle comprising one or more of the following amide moiety in the ring:

[Chem. 11]

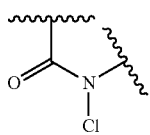

(Item 5)

The process of any one of Items 1 to 4, wherein the chlorinating agent is selected from the group consisting of trichloroisocyanuric acid, N-chlorosuccinimide, and 1,3-dichloro-5,5-dimethylhydantoin.

(Item 6)

The process of any one of Items 1 to 5, wherein the amount of the chlorinating agent ranges from 0.3 to 3 equivalents relative to a compound of Formula II.

(Item 7)

The process of any one of Items 1 to 6, wherein the activating agent is selected from the group consisting of the compounds of Formulae III, IV, and V:

[Chem. 12]

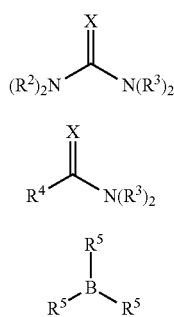

wherein $R^2$ and $R^3$ are each independently selected from the group consisting of hydrogen, $C_{1-6}$ alkyl, and $C_{6-14}$ aryl and each of $R^2$ or $R^3$ is independent; or alternatively, one of $R^2$ and one of $R^3$ may be combined to form a 5 or 6-membered heteromonocycle;

$R^4$ is selected from the group consisting of $C_{1-6}$ alkyl and $C_{6-14}$ aryl;

$R^5$ is $C_{1-6}$ alkoxy; and

X is O or S.

(Item 8)

The process of Item 7, wherein $R^2$ and $R^3$ are each independently selected from the group consisting of hydrogen, $C_{1-6}$ alkyl, and $C_{6-14}$ aryl and each of $R^2$ or $R^3$ is independent; or alternatively, one of $R^2$ and one of $R^3$ may be combined to form a saturated 5 or 6-membered heteromonocycle containing two nitrogen atoms.

(Item 9)

The process of either of Item 7 or 8, wherein the activating agent is selected from the compound of Formula III or IV.

(Item 10)

The process of Item 9, wherein the activating agent is selected from the compound of Formula III or IV wherein X is S.

(Item 11)

The process of Item 7, wherein the activating agent is selected from the group consisting of urea, thiourea, thioacetamide, thiobenzamide, N-methylthiourea, 1,3-dimethylthiourea, 2-imidazolidinethione, N-methylthioacetamide, benzamide, and (iPrO) 3B.

(Item 12)

The process of any one of Items 7 to 11, wherein the amount of the activating agent is in the range of 1 and 10 mol %.

(Item 13)

The process of Item 1, wherein $R^1$ is selected from $C_{1-6}$ alkoxymethyl, $C_{1-6}$ alkoxycarbonyl, benzyl, phenyloxymethyl which may be optionally substituted with at least one halogen atom, and tetrahydropyranyl;

the chlorinating agent is selected from the group consisting of trichloroisocyanuric acid, N-chlorosuccinimide, and 1,3-dichloro-5,5-dimethylhydantoin; and the activating agent is selected from the group consisting of the compounds of Formulae III, IV, and V:

[Chem. 13]

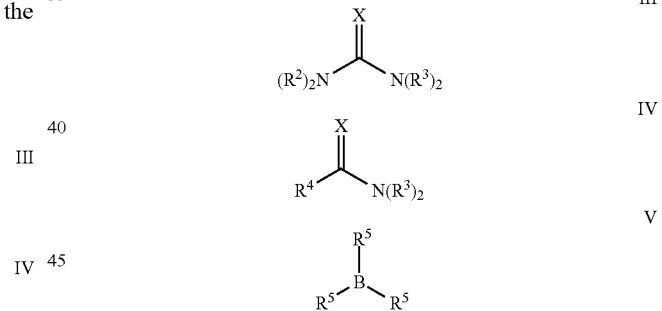

wherein $R^2$ and $R^3$ are each independently selected from the group consisting of hydrogen, $C_{1-6}$ alkyl, and $C_{6-14}$ aryl and each of $R^2$ or $R^3$ is independent; or alternatively, one of $R^2$ and one of $R^3$ may be combined to form a saturated 5 or 6-membered heteromonocycle containing two nitrogen atoms;

$R^4$ is selected from the group consisting of $C_{1-6}$ alkyl and $C_{6-14}$ aryl;

$R^5$ is $C_{1-6}$ alkoxy; and

X is O or S.

(Item 14)

The process of any one of Items 1 to 13, wherein the chlorination is conducted in a solvent selected from the group consisting of esters, nitriles, halogenated hydrocarbons, and any mixtures thereof.

(Item 15)

The process of any one of Items 1 to 14, wherein a dechlorinating agent is added after the chlorination of a compound of Formula II.

(Item 16)

The process of any one of Items 1 to 15, further comprising the step of deprotecting the compound of Formula I to give 2-chloro-4-nitroimidazole.

(Item 17)

A compound of Formula Ia:

[Chem. 14]

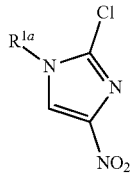

Ia wherein $R^{1a}$ is selected from $C_{1-6}$ alkoxymethyl, $C_{1-6}$ alkoxycarbonyl, phenyloxymethyl, and tetrahydropyranyl, each of which may be optionally substituted with at least one halogen atom.

(Item 18)

The compound of Item 17, wherein $R^{1a}$ is selected from ethoxymethyl, tert-butoxycarbonyl, 3-Cl-phenyloxymethyl, and tetrahydropyranyl.

Definitions

The term "halogen atom" used herein includes, for example, fluorine, chlorine, bromine, and iodine.

The term "$C_{1-6}$ alkyl" used herein denotes a straight or branched chain alkyl group having 1 to 6 carbon atom(s) and may constitute a part of other groups. The term specifically includes, for example, methyl, ethyl, n-propyl, iso-propyl, n-butyl, iso-butyl, sec-butyl, tert-butyl, n-pentyl, iso-pentyl, neopentyl, 2-methylpropyl, 1,1-dimethylpropyl, 1-ethylpropyl, n-hexyl, iso-hexyl, 3-methylpentyl, 1,1-dimethylbutyl, 2,2-dimethylbutyl, 3,3-dimethylbutyl, and 2-ethylbutyl. In some embodiments, $C_{1-6}$ alkyl may be methyl, ethyl, n-propyl or tert-butyl.

The term "$C_{1-6}$ alkoxy" used herein denotes a straight or branched chain alkoxy group having 1 to 6 carbon atom(s) and may constitute a part of other groups. The term specifically includes, for example, methoxy, ethoxy, n-propoxy, iso-propoxy, n-butoxy, iso-butoxy, sec-butoxy, tert-butoxy, n-pentyloxy, iso-pentyloxy, neopentyloxy, n-hexyloxy, iso-hexyloxy, and 3-methylpentyloxy.

The term "$C_{1-6}$ alkanoyl" used herein denotes a carbonyl group substituted with the above-defined "$C_{1-6}$ alkyl" and may constitute a part of other groups.

The term "$C_{6-14}$ aryl" used herein denotes a mono-, bi- or tri-cyclic aromatic hydrocarbon group having 6 to 14 carbon atoms and may constitute a part of other groups. The term specifically includes, for example, phenyl, naphthyl, anthryl, fluorenyl, and phenanthryl. In some embodiments, aryl may be $C_{6-10}$ aryl. In other embodiments, $C_{6-14}$ aryl may be phenyl.

The term "aralkyl" used herein denotes a straight or branched chain alkyl group having at least one, preferably 1 to 3, carbon atoms which are substituted with mono-, bi-, or tri-cyclic aromatic hydrocarbon groups and may constitute a part of other groups. In some embodiments, aralkyl may be $C_{6-14}$ aralkyl. An exemplary aralkyl includes benzyl, 1-phenylethyl, 2-phenylethyl, 1-naphthylmethyl, and 2-naphthylmethyl.

The term "chlorinating agent" used herein denotes a 5 to 7-membered heterocycle comprising one or more of the following chloroimide or amide moiety in the ring:

[Chem. 15]

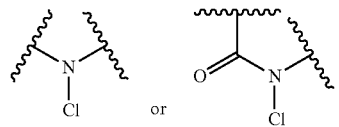

which can chlorinate 4-nitroimidazoles. An exemplary chlorinating agent specifically includes trichloroisocyanuric acid, N-chlorosuccinimide, and 1,3-dichloro-5,5-dimethylhydantoin.

The term "heteromonocycle" or "heteromonocyclyl" used herein denotes a 5 to 7-membered heteromonocyclyl ring or group that may be saturated or partially unsaturated, the ring or group comprising at least one nitrogen atom, and optionally further comprising at least one heteroatom selected from oxygen or sulfur. An exemplary heteromonocycle includes pyrrolidine, piperidine, azepane, imidazoline, imidazolidine, dihydrotriazine, triazacyclohexane, oxazolidine, morpholine, thiazolidine, and dihydrothiazine. In some embodiments, the heteromonocycle or heteromonocyclyl may be optionally substituted with at least one group selected from chloro or oxo. In other embodiments, the heteromonocycle or heteromonocyclyl is a saturated 5 or 6-membered heteromonocycle comprising at least one, preferably two or three, nitrogen atoms.

The term "alkali metal hydroxides" used herein includes sodium hydroxide, potassium hydroxide, and cesium hydroxide.

The term "alkali metal hydrides" used herein includes sodium hydride, potassium hydride, and cesium hydride.

The term "alkali metal carboxylates" used herein includes sodium acetate, potassium acetate, and sodium butyrate.

The term "alkali metal carbonates" used herein includes sodium carbonate, potassium carbonate, cesium carbonate, and lithium carbonate.

The term "alkali metal hydrogencarbonates" used herein includes sodium hydrogencarbonate, potassium hydrogencarbonate, and cesium hydrogencarbonate.

The term "alkali metal phosphates" used herein includes sodium phosphate, and potassium phosphate.

The term "alkali metal hydrogenphosphates" used herein includes sodium hydrogenphosphate, potassium hydrogenphosphate, and cesium hydrogenphosphate.

The term "aromatic amines" used herein includes pyridine and lutidine.

The term "tertiary amines" include triethylamine, tripropylamine, tributylamine, diisopropylethylamine, cyclohexyldimethylamine, 4-dimethylaminopyridine, N,N-dimethylaniline, N-methylpiperidine, N-methylpyrrolidine, N-methylmorpholine, tetramethylethylenediamine, tetramethylpropylenediamine, and 1,8-diazabicyclo[5,4,0]undec-7-ene (diazabicycloundecene).

The term "metal amides" used herein includes lithium diisopropylamide and lithium hexamethyldisilazide.

The term "metal alkoxides" used herein includes sodium methoxide, sodium ethoxide, sodium tert-butoxide, potassium tert-butoxide, and sodium phenoxide.

The term "hydrocarbons" used herein includes aliphatic hydrocarbons such as hexane and pentane; alicyclic hydrocarbons such as cyclopentane and cyclohexane; and aromatic hydrocarbons such as benzene and toluene.

The term "halogenated hydrocarbons" used herein includes chloroform, dichloromethane, dichloroethane, and tetrachloroethane.

The term "alcohols" used herein includes methanol, ethanol, isopropanol, propanol, and tert-butanol.

The term "ethers" used herein includes chain ethers such as diethyl ether, diisopropyl ether, dibutyl ether, and diphenyl ether; and cyclyl ethers such as 1,4-dioxane and tetrahydrofurane.

The term "esters" used herein includes ethyl acetate, n-propyl acetate, and ethyl propionate.

The term "ketones" used herein includes acetone, methyl ethyl ketone, and methyl isobutyl ketone.

The term "amides" used herein includes N,N-dimethylformamide, N,N-dimethylacetamide, and N-methyl-2-pyrrolidone.

The term "nitriles" used herein includes acetonitrile and propionitrile.

The term "sulfoxides" used herein includes dimethylsulfoxide.

The term "activating agent" used herein denotes an additive that may be used in combination with a chlorinating agent in the chlorinating step. Such an activating agent may have any one of the following structures of Formulae III, IV, and V:

[Chem. 16]

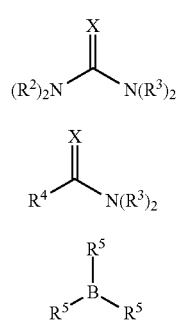

wherein $R^2$ and $R^3$ are each independently selected from the group consisting of hydrogen, $C_{1-6}$ alkyl, and $C_{6-14}$ aryl and each of $R^2$ or $R^3$ is independent; or alternatively, one of $R^2$ and one of $R^3$ may be combined to form a 5 or 6-membered heteromonocycle;

$R^4$ is selected from the group consisting of $C_{1-6}$ alkyl and $C_6$-14 aryl;

$R^5$ is $C_{1-6}$ alkoxy; and

X is O or S. The 5 or 6-membered heteromonocycle includes, for example, a saturated or partially unsaturated 5 or 6-membered heteromonocyclyl ring containing two or three nitrogen atoms in the ring. An exemplary 5 or 6-membered heteromonocycle in the activating agent includes imidazolidine, dihydrotriazine, or triazacyclohexane. An exemplary activating agent includes urea, thiourea, thioacetamide, thiobenzamide, N-methylthiourea, 1,3-dimethylthiourea, 2-imidazolidinethione, N-methylthioacetamide, benzamide, and $(iPrO)_3B$.

The term "dechlorinating agent" used herein denotes any agents that may reduce the generation of by-products, in particular di-chlorinated by-products, in the chlorination reaction and may increase the yield of mono-chlorinated products. An exemplary dechlorinating agent includes sodium sulfite and sodium thiosulfate.

General Procedure

2-Chloro-4-nitroimidazole derivatives represented by Formula I may be prepared by chlorination of N-protected 4-nitroimidazoles represented by Formula II. The N-protected 4-nitroimidazoles may be prepared by protection of 4-nitroimidazole. The 2-chloro-4-nitroimidazole derivatives may be deprotected to produce 2-chloro-4-nitroimidazole which is a useful intermediate in the preparation of Delamanid. In some embodiments, a series of the reactions is illustrated in Scheme 1. The processes of the present invention, however, are not limited thereto.

Scheme 1: Preparation of 2-chloro-4-nitroimidazole

[Chem. 17]

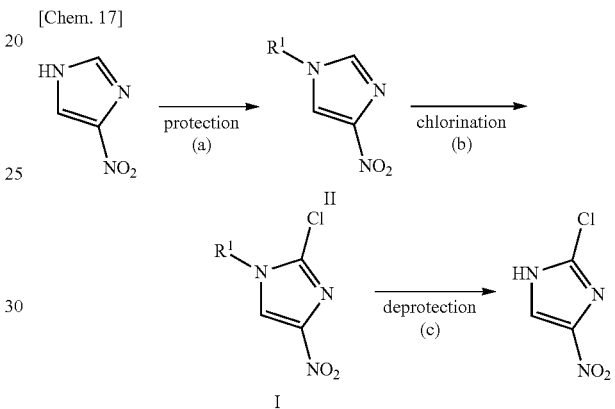

In the scheme, $R^1$ has the same meaning as defined in Item 1.

In step (a), N-protected 4-nitroimidazole of Formula II may be prepared by protecting 4-nitroimidazole with a protecting group, $R^1$, on the nitrogen atom at position 1 in the reaction with $R^1$—$X^1$, wherein $X^1$ is a suitable leaving group such as a halogen atom, in an inert solvent in the presence of a base. A suitable N-protecting group for 4-nitroimidazole may improve selectivity of chlorination and the yields of chlorination products as well as the yields of deprotected products in the subsequent steps. In some embodiments, $R^1$ includes, for example, $C_{1-6}$ alkoxy-$C_{1-6}$ alkyl group such as $C_{1-6}$ alkoxymethyl; $C_{1-6}$ alkoxy-$C_{1-6}$ alkoxy-$C_{1-6}$ alkyl such as 2-methoxyethoxymethyl (MEM); $C_{1-6}$ alkanoyloxymethyl group such as pivaloyloxymethyl; $C_{6-14}$ aralkyl group such as benzyl; $C_{6-10}$ aryloxy-$C_{1-6}$ alkyl such as phenoxymethyl; $C_{1-6}$ alkoxycarbonyl such as tert-butoxycarbonyl (Boc); $C_{6-14}$ aralkyloxycarbonyl such as benzyloxycarbonyl (Cbz); $C_{6-10}$ arylcarbonyl such as benzoyl; $C_{1-6}$ alkylsulfonyl such as methanesulfonyl; and $C_{1-6}$ alkyl-$C_{6-10}$ arylsulfonyl such as p-toluenesulfonyl, each of which may be optionally substituted with at least one halogen atom, particularly one to three halogen atoms. In some embodiments, $X^1$ is preferably selected from the group consisting of fluoro, chloro, bromo, and iodide.

In step (a), $R^1$ may be also introduced to 4-nitroimidazole in any alternative manners known in the art. For example, a compound of Formula II wherein $R^1$ is tetrahydropyranyl (THP) may be prepared by reaction of 4-nitroimidazole with dihydropyran.

Alternatively, 4-nitroimidazole may be reacted with a dimer derivative, R—$X^2$—R wherein R is $C_{1-6}$ alkoxy or $C_{1-6}$ alkoxycarbonyl and $X^2$ is —$CH_2$— or —O—, instead of $R^1$—$X^1$, to give a compound of Formula II. In some embodiments, R—$X^2$—R is diethoxymethane or $Boc_2O$.

A protecting reagent, $R^1$—$X^1$ or R—$X^2$—R, may be suitably selected in terms of the stability of a protecting group during the chlorination step (b) because the chlorination reaction may take a relatively long time (e.g. 24 hours or more). In some embodiments, the protecting group, $R^1$, may be easily removable in the deprotection step (c).

The base used in step (a) includes, for example, alkali metal hydroxides, alkali metal hydrides, alkali metal carbonates, alkali metal hydrogencarbonates, alkali metal hydrogenphosphates, aromatic amines, tertiary amines, metal amides, metal alkoxides, and may be a mixture of any two or more of them in an appropriate ratio. The amount of the base used may be typically 1 to 10 molar equivalents, preferably 1 to 5 molar equivalents, relative to 4-nitroimidazole. In some embodiments, sodium hydride, potassium carbonate, or triethylamine is used in this step.

The inert solvent used in this step includes, for example, hydrocarbons, halogenated hydrocarbons, ethers, esters, ketones, alcohols, water, amides, nitriles, and sulfoxides, and may be a mixture of any two or more of them in an appropriate ratio. In some embodiments, dichloromethane, tetrahydrofuran, ethyl acetate, dimethylformamide, or acetonitrile is used in this step.

The reaction temperature in this step may be, for example, in the range of 20° C. and 110° C. The reaction time in this step may be, for example, between 0.5 hour and 16 hours.

In step (b), a compound of Formula I may be prepared by chlorinating a compound of Formula II with a chlorinating agent in an inert solvent in the presence of an activating agent. In some embodiments, a compound of Formula II wherein $R^1$ is selected from the group consisting of $C_{1-6}$ alkoxymethyl, benzyl, THP, $C_{1-6}$ alkoxycarbonyl, and phenyloxymethyl which may be optionally substituted with at least one halogen atom, particularly one to three halogen atoms, is used. In other embodiments, a compound of Formula II wherein $R^1$ is selected from $C_{1-6}$ alkoxymethyl, benzyl, THP, Boc, or 3-Cl-phenoxymethyl is used. In still other embodiments, a compound of Formula II wherein $R^1$ is methoxymethyl, ethoxymethyl, or propoxymethyl is used.

The chlorinating agent used in this step may improve the selectivity or reactivity of chlorination. In some embodiments, the chlorinating agent is a 5 to 7-membered heteromonocycle comprising one or more of the following amide moiety in the ring:

[Chem. 18]

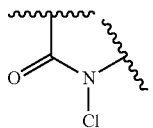

The chlorinating agent includes, specifically, trichloroisocyanuric acid (TCICA), N-chlorosuccinimide (NCS), and 1,3-dichloro-5,5-dimethylhydantoin (DCDMH). In some embodiments, the chlorinating agent is a 5 or 6-membered heteromonocycle comprising one or more, preferably two or three, of the chloroimide moiety or the amide moiety. An example of such a chlorinating agent is TCICA or DCDMH. In other embodiments, the chlorinating agent is TCICA. In some embodiments, the amount of the chlorinating agent ranges from 0.3 to 3 equivalents relative to a compound of Formula II. The amount of the chlorinating agent may be adjusted to include the stoichiometric amount or more of chlorine, for example, 1 to 3 equivalents of chlorine, in the chlorinating agent relative to a compound of Formula II. When a chlorinating agent comprises two chlorine atoms in its molecule, the amount of the chlorinating agent may, for example, be 0.5 to 2 equivalents relative to a compound of Formula II. When a chlorinating agent comprises three chlorine atoms in its molecule, the amount of the chlorinating agent may, for example, be 0.3 to 2 equivalents relative to a compound of Formula II. When TCICA where three chlorine atoms are comprised in a single molecule is used, 0.3 to 2 equivalents of TCICA may, for example, be added relative to the amount of a compound of Formula II. In some embodiments, the amount of TCICA is 0.5 to 0.8 equivalents.

The chlorination step (b) may be carried out in the presence of an activating agent to enhance the electropositive property of chlorine of a chlorinating agent and improve the selectivity of chlorination or reactivity of a compound of Formula II. In some embodiments, the activating agent is selected from the compound of Formula III or IV. In other embodiments, the activating agent is selected from the compound of Formula III wherein at least one of $R^2$ and $R^3$ is hydrogen or the compound of Formula IV wherein at least one of $R^3$ is hydrogen. In still other embodiments, the activating agent is selected from the compound of Formula III or IV wherein X is S. In still other embodiments, the activating agent includes urea, thiourea, thioacetamide, thiobenzamide, N-methylthiourea, 1,3-dimethylthiourea, 2-imidazolidinethione, N-methylthioacetamide, benzamide, and $(iPrO)_3B$. In still other embodiments, the activating agent includes thiourea, thioacetamide, thiobenzamide, N-methylthiourea, 1,3-dimethylthiourea, 2-imidazolidinethione, and N-methylthioacetamide. In still other embodiments, the activating agent includes thiourea, thiobenzamide, N-methylthiourea, 1,3-dimethylthiourea, and 2-imidazolidinethione. The amount of the activating agent may be, for example, in the range of 0.1 and 100 mol % per a compound of Formula II. In some embodiments, the amount of the activating agent is in the range of 1 and 10 mol %.

The use of an activating agent may accelerate the reaction rate and enhance the regioselectivity of the chlorination reaction to reduce unreacted starting materials or the generation of by-products such as N-substituted 5-chlorinated and 2,5-dichlorinated nitroimidazoles. In some embodiments, the use of the activating agent may reduce the generation of by-products by up to 20%. In other embodiments, the use of the activating agent may reduce the generation of by-products by up to 10%.

This step may be conducted in a suitable solvent. Such a solvent includes, for example, esters, nitriles, halogenated hydrocarbons, and any mixtures thereof. In some embodiments, the solvent may be selected from the group consisting of ethyl acetate, n-propyl acetate, acetonitrile, dichloroethane, tetrachloroethane, and any mixtures thereof. In other embodiments, the solvent in this step is ethyl acetate, acetonitrile, dichloroethane, or any mixtures thereof. The amount of the solvent may be, for example, in the range of 3 and 20 volume parts per 1 weight part of the starting substrate (i.e., a compound of formula II), hereinafter marked as 3 to 20 V (i.e., mL/g of the starting substrate). A preferable amount of the solvent may be in the range of 5 and 15 V. More preferably, the amount of the solvent may be in the range of 7 and 13 V. The solvent used in this step may be dry and the content of water in the solvent may be, for example, 0.5% or less, and preferably 0.1% or less.

The reaction temperature in step (b) may be, for example, in the range of room temperature and 150° C. A preferable reaction temperature may be in the range of 60° C. and 80° C., more preferably in the range of 60° C. and 70° C.

The reaction time in step (b) may be, for example, between 2 hours and 48 hours. A preferable reaction time may be between 14 hours and 24 hours.

The chlorination step (b) may be preferably conducted under conditions where a compound of Formula II may be selectively and reactively chlorinated and the generation of by-products, e.g. N-protected 5-chloro-4-nitroimidazole and N-protected 2,5-dichloro-4-nitroimidazole, may be suppressed. A combination of the chlorinating agent and the activating agent may provide good regioselectivity and reactivity in the chlorination and less generation of by-products in this step. In some embodiments, a combination of TCICA and thiourea are used. Addition of a dechlorinating agent, such as sodium sulfite ($Na_2SO_3$), after the chlorination in this step may also reduce the generation of the by-products, in particular a di-chlorinated by-product.

In step (c), 2-chloro-4-nitroimidazole (2-CNI) may be prepared by deprotecting a compound of Formula I. This step may be conducted under an acidic condition, i.e., in the presence of an acid. Such an acid includes, for example, an aqueous hydrochloric acid, trifluoroacetic acid (TFA), and sulfuric acid. A preferable acid may be a concentrated hydrochloric acid.

The reaction temperature in this step may be, for example, in the range of room temperature and 150° C. A preferable reaction temperature may be in the range of 70° C. and 110° C. The reaction time in this step may be, for example, between 1 hour and 24 hours. A preferable reaction time may be between 1 hour and 5 hours.

The process for preparing 2-chloro-4-nitroimidazole derivatives may further comprise a conventional purification step (d) after the deprotection step (c).

[Chem. 19]

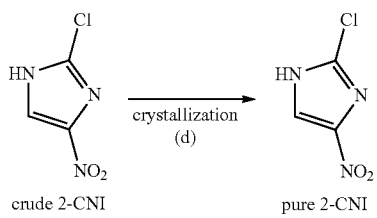

crude 2-CNI → (crystallization (d)) → pure 2-CNI

The purification step (d) may be conducted according to any conventional methods such as crystallization, optionally in combination with adsorption with a resin. Such a resin may be any resin that may adsorb or remove impurities such as unreacted starting materials and by-products. An exemplary resin specifically includes an ion-exchange resin and a synthetic adsorbent resin. In some embodiments, such a resin may be Amberlite™ XAD4, Amberlite™ XAD7HP, and Amberlyst™ A21, which may be obtained from commercial sources (e.g. The Dow Chemical Company and Sigma-Aldrich Co. LLC.).

Abbreviations used herein are shown below.
NIM: 4-nitroimidazole
2-CNI: 2-chloro-4-nitroimidazole
5-CNI: 5-chloro-4-nitroimidazole
2,5-DCNI: 2,5-dichloro-4-nitroimidazole
DCNI: dichloronitroimidazole
EM-NIM: 1-ethoxymethyl-4-nitroimidazole
EM-CNI: 1-ethoxymethyl-2-chloro-4-nitroimidazole
EM-5-CNI: 1-ethoxymethyl-5-chloro-4-nitroimidazole
EM-2,5-DCNI: 1-ethoxymethyl-2,5-dichloro-4-nitroimidazole
THP: tetrahydropyranyl
TCICA: trichloroisocyanuric acid
NCS: N-chlorosuccinimide
DCDMH: 1,3-dichloro-5,5-dimethylhydantoin
Ac: acetyl
Boc: tert-butoxycarbonyl
Cbz: benzyloxycarbonyl
Tos: p-toluenesulfonyl
Ms: methanesulfonyl
Bn: benzyl
Bz: benzoyl
ACN: acetonitrile
MeCN: acetonitrile
EtOAc: ethyl acetate
DCE: dichloroethane
CPME: cyclopentylmethyl ether
MeOAc: methyl acetate
EtOAc: ethyl acetate
n-PrOAc: n-propyl acetate
OctOAc: octyl acetate
THF: tetrahydrofuran
EtOH: ethanol
DMAc: dimethyl acetamide
DMSO: dimethyl sulfoxide
DMF: dimethylformamide
NMP: N-methyl-2-pyrrolidone
DHP: dihydropyran
TFA: trifluoroacetic acid
TEA: triethylamine
DMAP: 4-dimethylaminopyridine

EXAMPLES

Specific processes for preparing 2-chloro-4-nitroimidazole derivatives are illustrated as an example as shown below. The present invention is not intended to be limited by the following examples.

NMR spectra were measured on FT-NMR spectrometer BRUKER AVANCE (600 MHz, $^1$H at 600.17 MHz, and $^{13}$C at 150.04 MHz) in $CD_3OD$ at 25° C.

Mass spectra were measured on SQD2 spectrometer WATERS.

HPLC conditions are shown as follows.
Mobile Phase:
  MF A: Methanol/Water/Phosphoric acid; 150/850/2 ml
  MF B: Acetonitrile
Solvent for sample: Methanol
Hplc Conditions:
  Column: Purospher STAR C18, 150×4.6 mm, 5 μm
  Flow rate: 1 ml/min
  Injection: 5 μl
  Duration: 35 min
  Delay: 10 min
  Wave length: 220 nm
  Column temperature: 30° C.
Gradient Elution:

TABLE 1

| Time (min) | % MF A | % MF B |
| --- | --- | --- |
| 0 | 100 | 0 |
| 8 | 100 | 0 |

TABLE 1-continued

| Time (min) | % MF A | % MF B |
|---|---|---|
| 20 | 30 | 70 |
| 30 | 30 | 70 |
| 30.02 | 100 | 0 |
| 35 | 100 | 0 |

Example 1: Syntheses of N-Protected 4-nitroimidazoles

1-Boc-4-nitroimidazole (Boc-NIM) was synthesized by the reaction of 4-nitroimidazole (20 g) with Boc$_2$O (42.4 g) at presence of DMAP (2.16 g). The reaction was carried out in dichloromethane (300 ml) at ambient temperature. After extraction with diluted citric acid the organic phase was evaporated to afford desired Boc-NIM in 96% yield.

ES-MS calculated for $C_8H_{11}N_3O_4$ 213.19 [M–H$^+$]$^+$. found 214.10.

1-THP-4-nitroimidazole (THP-NIM) was synthesized by the reaction of 4-nitroimidazole (11.3 g) with dihydropyrane (18.3 ml) at presence of p-toluenesulfonic acid (0.5 g) as a catalyst. The reaction was carried out in ethylacetate (200 ml) at ambient temperature. After quench by trimethylamine (0.35 ml) the reaction mixture was filtered and evaporated to afford crude THP-NIM. The product was purified by crystallization with acetonitrile/hexane to afford 54% of THP-NIM.

ES-MS calculated for $C_8H_{11}N_3O_{03}$ 197.19 [M–H$^+$]$^+$. found 198.12.

1-(3-Cl-PhO—CH$_2$)-4-NIM was synthesized by the reaction of 4-nitroimidazole (1.13 g) with 3-Cl-PhO—CH$_2$-chloride (2.3 g) at presence of trimethylamine (1.67 ml). The reaction was carried out in ethylacetate (10 ml) at ambient temperature. After extraction with water the organic phase was evaporated to afford desired product in 74% yield.

ES-MS calculated for $C_{10}H_8ClN_3O_3$ 253.0, [M+H$^+$]$^+$. found 254.0.

Example 2: Synthesis of 1-Ethoxymethyl-4-nitroimidazole (EM-NIM)

Diethoxymethane (197.6 g) and ZnBr$_2$ (0.57 g) were placed to dry reaction vessel and cooled down to 10° C. AcCl (129 g) was added slowly to the reaction mixture over period of 0.5-1 h while the temperature did not exceed 40° C. and then stirred for 0.5 h. NIM (143 g) and EtOAc (830 ml) were added and the reaction mixture was stirred for 15 min. Then Et$_3$N (212 ml) was added slowly over period of 0.5-1 h while the temperature did not exceed 40° C. and stirred for 15 min. Then the reaction mixture was stirred for 1 h at 70° C. After cooling to 40° C. another portion of Et$_3$N (35 ml) was added slowly. Then the reaction mixture was filtered over Celite (registered trade mark), water was added and extracted twice with EtOAc. Evaporation of the organic phases afforded EM-NIM.

ES-MS calculated for $C_6H_9N_3O_3$ 171.15 [M–H$^+$]$^+$. found 172.08.

Example 3: Effect of Protecting Groups in Chlorination

Several protecting groups were investigated.

[Chem. 20]

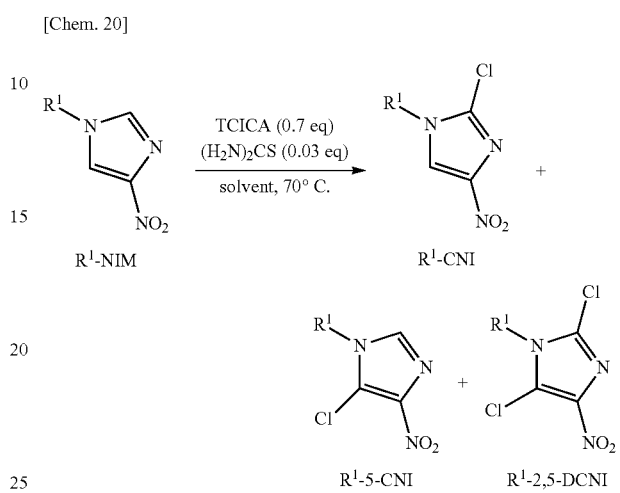

In the scheme, the equivalent amounts are those relative to the starting material, R$^1$-NIM.

TCICA (0.7 equiv) and thiourea (0.03 equiv) were added to a solution of R$^1$-4-nitroimidazole (1 equiv) in solvent (8V). The reaction vessel was tightly closed and the resulting mixture was maintained under stirring at 70° C. for 18 hrs. After cooling and filtration over Celite (registered trade mark), an aliquot of the solution was evaporated and used for HPLC measurement.

TABLE 2

Chlorination of variously protected 4-nitroimidazole-composition of the reaction mixture

| | HPLC of crude RM (% of area) | | |
|---|---|---|---|
| Protecting groups | R$^1$-CNI | R$^1$-5-CNI | R$^1$-2,5-DCNI |
| Examples | | | |
| Ethoxymethyl | 61 | 2 | 4 |
| Benzyl | 42 | 18 | 10 |
| THP | 54 | 20 | 7 |
| Boc | 40 | 18 | 3 |
| 3-Cl—PhO—CH$_2$— | 49 | 9 | 7 |
| Comparative Example | | | |
| H | 2 | 0.4 | n.o. | n.o. = not observed

Example 4: Effect of Chlorinating Agents in Chlorination

The influence of a chlorinating agent was screened. Three chloroimide compounds were investigated as potentially suitable agent for direct chlorination as shown below.

[Chem. 21]

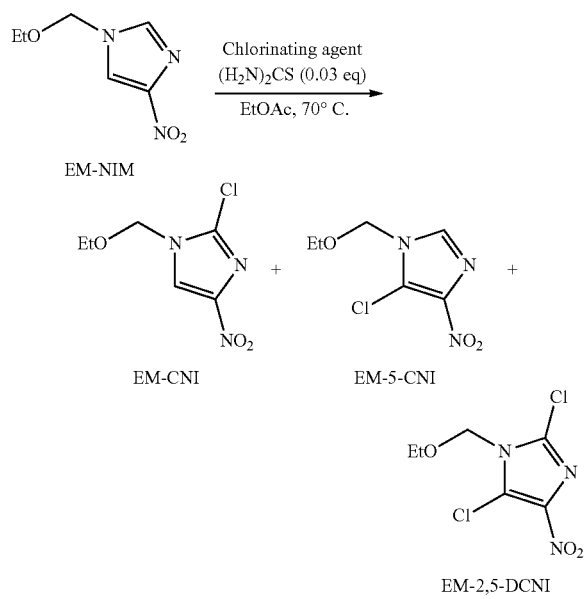

In the scheme, the equivalent amounts are those relative to the starting material, EM-NIM.

A chlorinating agent selected from TCICA: 0.7 equiv, NCS: 2 equiv, or DCDMH: 1 equiv and thiourea (0.03 equiv) were added to a solution of N-ethoxymethyl-4-nitroimidazole (1 equiv) in ethyl acetate (8 V). The reaction vessel was tightly closed and the resulting mixture was maintained under stirring at 70° C. for 18 hrs. After cooling and filtration over Celite (registered trade mark), aliquot of the solution was evaporated and used for HPLC measurement. When TCICA was used, HPLC measurement of the crude reaction mixture showed that 63% of EM-CNI, 3% of EM-5-CNI, and 4% of EM-2,5-DCNI were observed.

TABLE 3

| Compounds | NMR spectra |
|---|---|
| EM-CNI | $^1$H NMR (DMSO) δ 8.71 (s, 1H), 5.43 (s, 2H), 3.55 (q, 2H), 1.11 (t, 3H). $^{13}$C NMR (DMSO) δ 144.71, 131.89, 123.85, 76.37, 64.48, 14.57. |
| EM-5-CNI | $^1$H NMR (DMSO) δ 8.20 (s, 1H), 5.48 (s, 2H), 3.53 (q, 2H), 1.10 (t, 3H). $^{13}$C NMR (DMSO) δ 141.86, 136.57, 119.03, 75.01, 64.33, 14.58. |
| EM-2,5-DCNI | $^1$H NMR (CDCl$_3$) δ 5.47 (s, 2H), 3.60 (q, 2H), 1.13 (t, 3H). |

Example 5: Effect of Solvents in Chlorination

[Chem. 22]

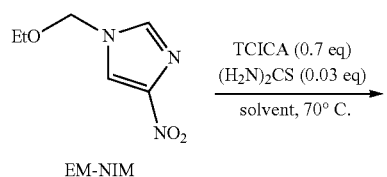

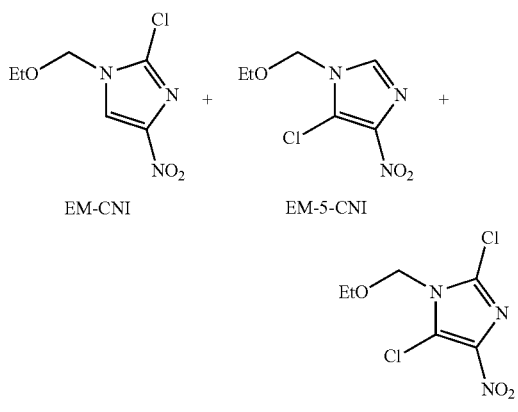

Several solvents were investigated. Among many solvents tested, acetonitrile, chlorinated solvents and esters provided the desired EM-CNI with good selectivity (see Table 4).

TCICA (0.7 equiv) and thiourea (0.03 equiv) were added to a solution of N-ethoxymethyl-4-nitroimidazole (1 equiv) in solvent (8 V). The reaction vessel was tightly closed and the resulting mixture was maintained under stirring at 70° C. for 18 hrs. After cooling and filtration over Celite (registered trade mark), an aliquot of the solution was evaporated and used for HPLC measurement.

TABLE 4

Chlorination in different solvents - composition of the reaction mixture

| | HPLC of crude RM (% of area) | | |
|---|---|---|---|
| Solvent | EM-CNI | EM-5-CNI | EM-2,5-DCNI |
| EtOAc | 61 | 2 | 4 |
| DCE | 55 | 2 | 5 |
| MeCN | 55 | 2 | 6 |

Example 6: Effect of Activating Agents in Chlorination

[Chem. 23]

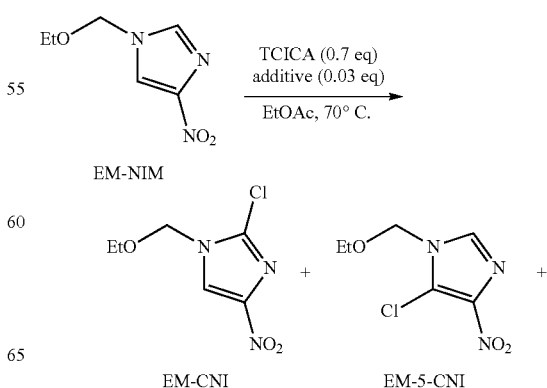

-continued

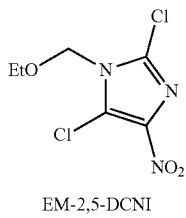

EM-2,5-DCNI

Several additives were tested. The results are summarized in Table 5.

TABLE 5

Chlorination using various activating agents - composition of the reaction mixture

| Activating agent | HPLC of crude RM (% of area) | | |
|---|---|---|---|
| | EM-CNI | EM-5-CNI | EM-2,5-DCNI |
| thiourea | 61 | 2 | 4 |
| benzamide | 32 | 8 | 3 |
| thiobenzamide | 51 | 1 | 4 |
| (iPrO)$_3$B [a] | 22 | 8 | 1 |
| urea [a] | 34 | 3 | 3 |

[a] 10 mol % of the additive was reacted.

Example 7: Synthesis of 2-chloro-4-nitro-1H-imidazole

Trichloroisocyanuric acid (3.25 g) and thiourea (46 mg) were added to a solution of N-ethoxymethyl-4-nitroimidazole (3.42 g) in ethyl acetate (25 ml). The reactor was tightly closed and the resulting mixture was maintained under stirring at 70° C. for 18 hrs. After cooling and filtration over Celite (registered trade mark), 20 ml of water was added. After separation of layers, aqueous phase was extracted 2× with ethyl acetate (10 ml). Collected organic extracts were evaporated under reduced pressure to afford 4.4 g of the crude product. Hydrochloric acid (5.3 ml) and water (5 ml) were then added and the resulting mixture was maintained under stirring at 70° C. for 3 hrs. After cooling to 50° C., methanol (7 ml) and 10 M sodium hydroxide solution (4 ml) were added dropwise. The suspension was stirred in an ice cooling bath for 2 hrs, then filtered and washed with methanol/water to afford 1.03 g (35%) of the desired 2-chloro-4-nitro-1H-imidazole. The product was recrystallized from MeOH/HCl/water to obtain 0.72 g (24%) of a pure 2-CNI.

$^1$H NMR (CD$_3$OD) δ 8.09 (s, 1H)
$^{13}$C NMR (CD$_3$OD) δ 147.8, 132.8, 120.6
ES-MS calculated for C$_3$H$_2$N$_3$O$_2$Cl 147.51 [M−H]$^-$. found 145.86.

Example 8: Synthesis of 2-chloro-4-nitro-1H-imidazole

Trichloroisocyanuric acid (40.67 g) and thiourea (0.57 g) were added to a solution of N-ethoxymethyl-4-nitroimidazole (42.79 g) in ethyl acetate (340 ml). The reactor was tightly closed and the resulting mixture was maintained under stirring at 70° C. for 18 hrs. After cooling and filtration over Celite (registered trade mark), the filtrate was evaporated to afford 58.9 g of an oily intermediate. Hydrochloric acid (33 ml) was then added and the resulting mixture was maintained under stirring at 60° C. for 3 hrs. After dilution of ethyl acetate (200 ml) and water (100 ml), pH was adjusted to 1-1.5 by addition of sodium hydroxide solution. The layers were separated and aqueous phase was extracted with ethyl acetate (2×60 ml). Collected organic extracts were evaporated under reduced pressure to afford 44.2 g of the crude product. Another hydrochloric acid (22 ml), water (11 ml) and methanol (80 ml) were added and the resulting mixture was heated to reflux. 80 ml of solvents was slowly distilled off and the obtained suspension was cooled to 20-25° C. Then, the mixture was stirred in an ice cooling bath for 2 hrs, filtered and washed with methanol/water to afford 11.4 g (31%) of the desired 2-chloro-4-nitro-1H-imidazole (HPLC purity: 99%).

$^1$H NMR (DMSO) δ 14.17 (s, 1H), 8.40 (s, 1H).
$^{13}$C NMR (DMSO) δ 145.90, 130.71, 121.10.

Example 9: Synthesis of 2-chloro-4-nitro-1H-imidazole

Trichloroisocyanuric acid (5.23 kg) and thiourea (73.4 g) were added to a solution of N-ethoxymethyl-4-nitroimidazole (5.5 kg) in ethyl acetate (55 L). The reactor was tightly closed and the resulting mixture was maintained under stirring at 65-70° C. for 16 hours. After cooling and filtration over Celite (registered trade mark), the filtrate was added to the solution of sodium sulfite (10.12 kg) in water (50 L) at 60-65° C. The layers were separated and the water phase was extracted once again with ethyl acetate (20 L). Combined organic extracts were evaporated under reduced pressure to afford 3.25 kg of the oily product. Hydrochloric acid (5.51 L) and water (3.67 L) were added and the resulting solution was heated to the reflux. Then 3.5 L of solvents were distilled off within 2 hours period and the mixture was slowly cooled to the ambient temperature. The crystallization was performed at stirring and maintaining temperature 0-5° C. for 8 hours. The suspension was filtered, washed with water (2×1.5 L) and dried at 60° C. to afford 1456 g (30.7%) of desired 2-chloro-4-nitro-1H-imidazole (HPLC purity: 99.75%).

$^1$H NMR (DMSO) δ 14.12 (s, 1H), 8.39 (s, 1H).
$^{13}$C NMR (CD$_3$OD) δ 145.87, 130.66, 121.05.

INDUSTRIAL APPLICABILITY

The processes for preparing 2-chloro-4-nitroimidazole derivatives disclosed herein may be useful for the industrial production of an anti-tuberculosis drug, delamanid, with low production costs.

The invention claimed is:
1. A process for preparing a compound of Formula I:

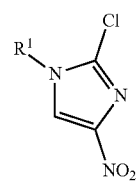

wherein R$^1$ is selected from the group consisting of C$_{1-6}$ alkoxy-C$_{1-6}$ alkyl, C$_{1-6}$ alkoxy-C$_{1-6}$ alkoxy-C$_{1-6}$ alkyl, C$_{1-6}$ alkanoyloxymethyl, C$_{6-14}$ aralkyl, C$_{6-10}$ aryloxy-C$_{1-6}$ alkyl, C$_{1-6}$ alkoxycarbonyl, C$_{6-10}$ arylcarbonyl, C$_{1-6}$ alkyl sulfonyl, C$_{1-6}$ alkyl-C$_{6-10}$ arylsulfonyl, and tetrahydropyranyl, each of which may be optionally substituted with at least one halogen atom, comprising chlorinating a compound of Formula II:

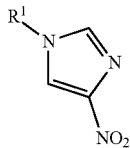

with a chlorinating agent and an activating agent to give a compound of Formula I.

2. The process of claim 1, wherein $R^1$ is selected from $C_{1-6}$ alkoxymethyl, $C_{1-6}$ alkoxycarbonyl, benzyl, phenyloxymethyl, and tetrahydropyranyl, each of which may be optionally substituted with at least one halogen atom.

3. The process of claim 1, wherein the chlorinating agent is a 5 or 6-membered heteromonocycle comprising one or more of the following chloroimide moiety in the ring:

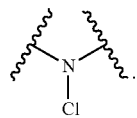 [SMILES: *N(*)Cl]

4. The process of claim 1, wherein the chlorinating agent is a 5 or 6-membered heteromonocycle comprising one or more of the following amide moiety in the ring:

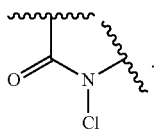 [SMILES: *C(=O)N(*)Cl]

5. The process of claim 1, wherein the chlorinating agent is selected from the group consisting of trichloroisocyanuric acid, N-chlorosuccinimide, and 1,3-dichloro-5,5-dimethylhydantoin.

6. The process of claim 1, wherein the activating agent is selected from the group consisting of the compounds of Formulae III, IV, and V:

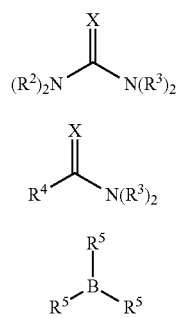

wherein $R^2$ and $R^3$ are each independently selected from the group consisting of hydrogen, $C_{1-6}$ alkyl, and $C_{6-14}$ aryl and each of $R^2$ or $R^3$ is independent; or alternatively, one of $R^2$ and one of $R^3$ may be combined to form a 5 or 6-membered heteromonocycle;

$R^4$ is selected from the group consisting of $C_{1-6}$ alkyl and $C_{6-14}$ aryl;

$R^5$ is $C_{1-6}$ alkoxy; and

X is O or S.

7. The process of claim 6, wherein $R^2$ and $R^3$ are each independently selected from the group consisting of hydrogen, $C_{1-6}$ alkyl, and $C_{6-14}$ aryl and each of $R^2$ or $R^3$ is independent; or alternatively, one of $R^2$ and one of $R^3$ may be combined to form a saturated 5 or 6-membered heteromonocycle containing two nitrogen atoms.

8. The process of claim 6, wherein the activating agent is selected from the compound of Formula III or IV.

9. The process of claim 8, wherein the activating agent is selected from the compound of Formula III or IV wherein X is S.

10. The process of claim 6, wherein the activating agent is selected from the group consisting of urea, thiourea, thioacetamide, thiobenzamide, N-methylthiourea, 1,3-dimethylthiourea, 2-imidazolidinethione, N-methylthioacetamide, benzamide, and (iPrO)$_3$B.

11. The process of claim 1, wherein $R^1$ is selected from $C_{1-6}$ alkoxymethyl, $C_{1-6}$ alkoxycarbonyl, benzyl, phenyloxymethyl which may be optionally substituted with at least one halogen atom, and tetrahydropyranyl;

the chlorinating agent is selected from the group consisting of trichloroisocyanuric acid, N-chlorosuccinimide, and 1,3-dichloro-5,5-dimethylhydantoin; and the activating agent is selected from the group consisting of the compounds of Formulae III, IV, and V:

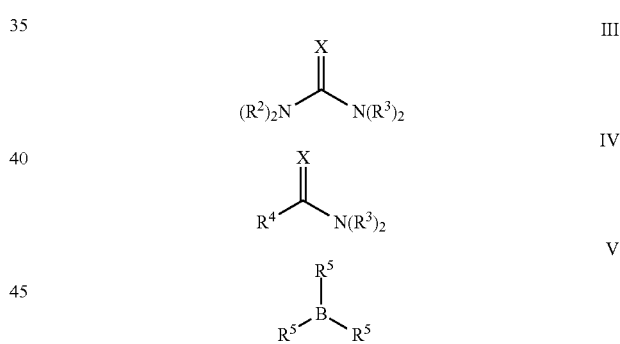

wherein $R^2$ and $R^3$ are each independently selected from the group consisting of hydrogen, $C_{1-6}$ alkyl, and $C_{6-14}$ aryl and each of $R^2$ or $R^3$ is independent; or alternatively, one of $R^2$ and one of $R^3$ may be combined to form a saturated 5 or 6-membered heteromonocycle containing two nitrogen atoms;

$R^4$ is selected from the group consisting of $C_{1-6}$ alkyl and $C_{6-14}$ aryl;

$R^5$ is $C_{1-6}$ alkoxy; and

X is O or S.

12. The process of claim 1, wherein the chlorination is conducted in a solvent selected from the group consisting of esters, nitriles, halogenated hydrocarbons, and any mixtures thereof.

13. The process of claim 1, wherein a dechlorinating agent is added after the chlorination of a compound of Formula II.

14. The process of claim 1, further comprising the step of deprotecting the compound of Formula I to give 2-chloro-4-nitroimidazole.

15. A compound of Formula Ia:
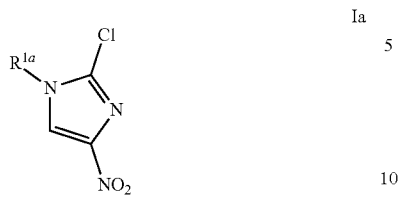
wherein $R^{1a}$ is selected from $C_{1-6}$ alkoxymethyl, $C_{1-6}$ alkoxycarbonyl, phenyloxymethyl, and tetrahydropyranyl, each of which may be optionally substituted with at least one halogen atom.
16. The compound of claim 15, wherein $R^{1a}$ is selected from ethoxymethyl, tert-butoxycarbonyl, 3-Cl-phenyloxymethyl, and tetrahydropyranyl.
* * * * *